United States Patent
Maye et al.

(10) Patent No.: US 8,632,789 B2
(45) Date of Patent: Jan. 21, 2014

(54) SYSTEM AND METHOD FOR DELIVERY OF DNA-BINDING CHEMOTHERAPY DRUGS USING NANOPARTICLES

(75) Inventors: Mathew Maye, Binghamton, NY (US); James Dabrowiak, Syracuse, NY (US); Colleen Alexander, Auburn, NY (US)

(73) Assignee: Syracuse University, Syracuse, NY (US)

( * ) Notice: Subject to any disclaimer, the term of this patent is extended or adjusted under 35 U.S.C. 154(b) by 16 days.

(21) Appl. No.: 13/286,847

(22) Filed: Nov. 1, 2011

(65) Prior Publication Data

US 2012/0141550 A1    Jun. 7, 2012

Related U.S. Application Data

(60) Provisional application No. 61/408,824, filed on Nov. 1, 2010.

(51) Int. Cl.
*A61K 9/14*    (2006.01)
*A61P 35/00*   (2006.01)
*B82B 1/00*    (2006.01)

(52) U.S. Cl.
USPC .......... 424/400; 428/402; 435/458; 536/23.1; 536/24.5

(58) Field of Classification Search
None
See application file for complete search history.

(56) References Cited

U.S. PATENT DOCUMENTS

| 7,332,586 B2 | 2/2008 | Franzen |
| 2006/0222595 A1 | 10/2006 | Mukherjee |
| 2007/0292495 A1 | 12/2007 | Ludwig et al. |
| 2008/0038686 A1 | 2/2008 | Nagai |
| 2009/0093551 A1* | 4/2009 | Bhatia et al. ................ 514/773 |
| 2009/0148535 A1* | 6/2009 | Bamdad ....................... 424/499 |

FOREIGN PATENT DOCUMENTS

WO    WO2009155431    12/2009

OTHER PUBLICATIONS

Huiming Zhang, PhD (2008) Thermally cross-linked superparamagnetic iron oxide nanoparticle-A10 RNA aptamer-doxorubicin conjugate. Molecular Imaging and Contrast Agent Database (MICAD) [Internet]. Bethesda (MD): National Center for Biotechnology Information (US); 2004-2012. Aug. 29, 2008 [updated Oct. 8, 2008].*
International Search Report Form PCT/ISA/220, International Application No. PCT/US2011/058805, pp. 1-7, Dated May 16, 2013.

* cited by examiner

*Primary Examiner* — Janet Epps-Smith
(74) *Attorney, Agent, or Firm* — David L. Nocilly; Bond Schoeneck & King, PLLC (57) ABSTRACT

System and method for loading the front line anticancer drug, doxorubicin (DOX) onto DNA-capped gold nanoparticles whose duplex DNA has been designed for specific DOX intercalation. Since each AuNP contains about 108 high affinity drug sites, this design allows for a high local DOX concentration on the particle. Drug binding was confirmed by monitoring the increase in DNA melting temperature, the shift in the plasmon resonance maximum, and the increase in the NP hydrodynamic radius as a function of [DOX]/[DNA] ratio. The feasibility of the nanoparticles as a drug delivery system was demonstrated by showing that particle-bound DOX could be transferred to a target DNA.

19 Claims, 7 Drawing Sheets

SYSTEM AND METHOD FOR DELIVERY OF DNA-BINDING CHEMOTHERAPY DRUGS USING NANOPARTICLES

CROSS-REFERENCE TO RELATED APPLICATIONS

This application claims priority to U.S. Provisional Patent Application Ser. No. 61/408,824 filed on Nov. 1, 2010 and entitled "System and Method for Delivery of Doxorubin Using Gold Nanoparticles," the entirety of which is hereby incorporated by reference herein

BACKGROUND OF THE INVENTION

1. Field of the Invention

The present invention relates to the delivery of pharmaceuticals and, more particularly, to the use of DNA-capped gold nanoparticles as a delivery mechanism.

2. Description of the Related Art

Metal compounds and complexes are widely used for treating and detecting disease and they are playing an increasingly important role in the emerging field of nanomedicine. Gold nanoparticles (AuNP) in particular offer a number of attractive features for visualization, detection, and treatment of disease. They exhibit a range of surface chemistries for drug or biomaterial modification and, when internalized by the cell, they appear to have minimally toxic effects. For example, DNA-capped AuNP has been used as intracellular gene regulation agents for the control of protein expression in cells, and platinum drugs conjugated to AuNP show considerable promise as chemotherotherapeutic agents. In addition to drug attachment, the NP core itself could be used in treatment strategies and one emerging approach is photothermal therapy, in which the particle is heated to cause damage to the cell.

Most clinically used anticancer drugs have relatively narrow therapeutic windows indicating that the distribution of the drug between normal and diseased tissue is small. For example, the anthracycline antibiotic doxorubicin (DOX, or adriamycin) is a clinically approved chemotherapy agent that binds to DNA via sequence specific intercalation. The binding mechanism involves intercalation of the aglycone portion of the drug at a high affinity site, e.g., 5'-CG/CG, with the daunosamine sugar lying in the minor groove, occluding an additional DNA base pair adjacent to the intercalation site. When bound to DNA, the drug inhibits the enzyme topoisomerase II and the action of DNA polymerase causing cell death. DOX intercalation stabilizes the double-helix, which has been shown to result in an increase in thermal denaturation (e.g. melting) temperature of duplex DNA.

BRIEF SUMMARY OF THE INVENTION

It is therefore a principal object and advantage of the present invention to provide a system and method for delivering doxorubicin.

In accordance with the foregoing objects and advantages, the present invention comprises a system and method for loading the front line anticancer drug, doxorubicin (DOX) onto DNA-capped gold nanoparticles whose duplex DNA has been designed for specific DOX intercalation. Drug binding was confirmed by monitoring the increase in DNA melting temperature, the shift in the plasmon resonance maximum, and the increase in the NP hydrodynamic radius as a function of [DOX]/[DNA] ratio.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
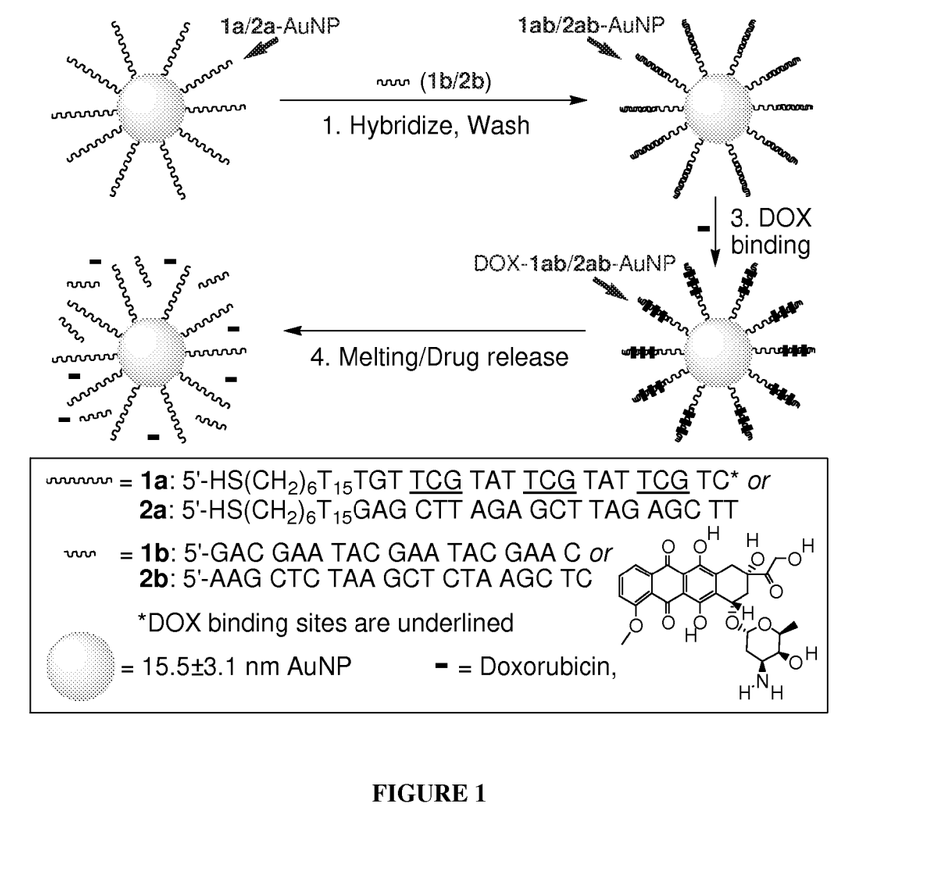
FIG. 1 is a schematic showing preparation, drug loading and release of doxorubicin according to the present invention.

Referring now to the drawings, wherein like reference numerals refer to like parts throughout, there is seen in FIG. 1 a system according to the presention invention that uses the sequence specificity of DOX and engineer two DNA-capped AuNPs, one capable of binding multiple copies of DOX with high affinity and a second having reduced binding for drug. The particles were prepared by covalently attaching multiple copies of a 5'-thiol-modified 35-mer oligonucleotide to the surface of 15.5±3.1 nm AuNP followed by hybridization of the complementary 19-mer, 1b or 2b, to yield 1ab/2ab-AuNP. The 1ab duplex was designed to include three identical high affinity DOX intercalation sites having the sequence, 5'-TCG. Binding sites were separated by a 3-nucleotide spacer, allowing each 1ab to simultaneously bind three DOX molecules. The duplex 2ab was designed to have length and melting characteristics similar to 1ab, but to lack high affinity DOX intercalation sites. In order to quantify the number of 1ab or 2ab at each AuNP (e.g. dsDNA), a fluorescently tagged 1b was employed, 1b-CY3. Fluorescence spectroscopy was then utilized to determine the quantity of 1b-CY3 hybridized at the 1a-AuNP. Using this approach an average number of 36±1 1ab/AuNP was measured. From this value and the spectrophotometrically determined concentration of AuNP, the value of, [DOX]/[1ab]=r, was determined for the various experiments. Considering that three binding sites exist per 1ab, one can expect ~108 high affinity DOX sites per AuNP.

The 1ab-AuNP (with [AuNP]=13.7 nM) were incubated with DOX, at r=0 to 12 for 40 min at RT in PBS (10 mM Phosphate buffer, 100 mM NaCl, pH=7.4), and separated from unbound drug by centrifugation. To probe the uptake of DOX via intercalation to 1ab-AuNP, we investigated the thermal denaturation of the 1ab strands by measuring increase in extinction at 260 nm using UV-visible spectroscopy (UV-vis). The melting of duplex DNA at NP interfaces is known to be influenced by a number of cooperative effects resulting from the confined DNA environment at the nano-interface, namely; increased local DNA concentration and ionic strengths. These effects are known to result in an increase in melting cooperativity, as well as an increase in $T_m$.

Figure 2:
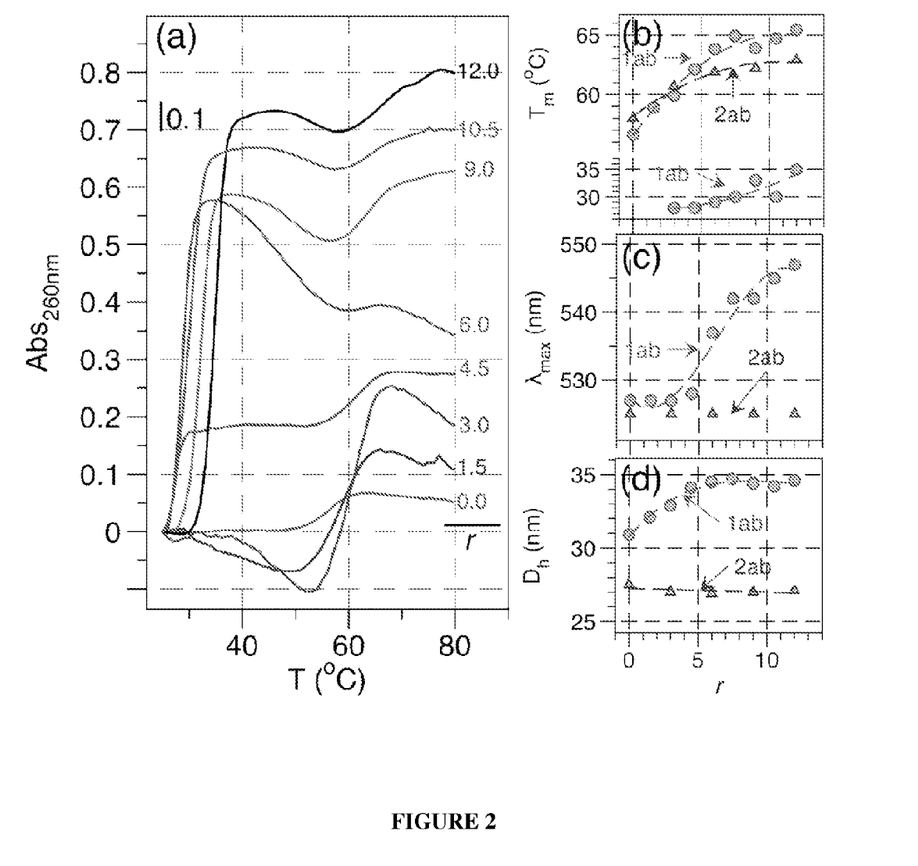
FIG. 2 is a series of graphs showing: (a) thermal denaturation plots obtained at 1° C./min for 1ab-AuNP at increasing [DOX]/[1ab] ratio, r=0-12, and the summary of $T_m$ (b), $\lambda_{SPR}$ (c), and $D_h$ (d) change with r, allowing for comparison between 1ab and 2ab, where melting profiles normalized and off-set for clarity only.

FIG. 2 shows the observed melting profiles as a function of r. At r=0, the 1ab-AuNP exhibits cooperative melting associated with duplex 1ab with $T_m$=56.6° C. However, upon addition of drug, the $T_m$ increases from 56.6 to 65.4° C. in the range, r=0 to ~6 (FIG. 1a). This is consistent with drug binding to DNA on 1ab-AuNP thereby increasing $T_m$. An interesting aspect of the melting profiles shown in FIG. 2a is the low $T_m$ feature between 28-35° C. when r>~3. This reversible melting feature appears to be the result of increased drug loading on the DNA and/or particle when all high affinity DOX sites on 1ab are saturated (r~3). This feature strongly correlates with the surface plasmon resonance band, $\lambda_{SPR}$, of the AuNP (FIG. 2c), which undergoes a $\lambda_{SPR}$ red shift from 527 to 547 nm at r>3. A red shift in $\lambda_{SPR}$ is indicative of a change in the dielectric medium immediately surrounding the AuNP, and/or interactions between AuNP as the result of assembly or clustering. Such clustering is likely the result of the increasingly hydrophobic nature of 1ab-AuNP at high r, which can approach ~300 if all DOX present is bound to AuNP.

Drug binding to 1ab-AuNP was also probed via dynamic light scattering (DLS). DLS measures the hydrodynamic diameter, $D_h$, of the 1ab-AuNP, which is influenced by both the diameter of AuNP as well as the thickness of the DNA shell. Since drug initially binds at each site on 1ab by intercalation, we can expect an increase in the length of 1ab by ~1 nm (3×3.6 Å), which would correlated with a net increase of ~2 nm in $D_h$. FIG. 2d shows a $D_h$ increase with r of about ~2 nm at r~3, and a net increase of ~4 nm at r>3. This observation is consistent with drug intercalation at r<~3 followed by less specific interaction at r>~3.

In order to better understand the interaction between DOX and 1ab-AuNP, parallel experiments were carried out with 2ab-AuNP which contains DNA sequences that more weakly bind drug. At r=0, the $T_m$ value for 2ab-AuNP is 58.0° C. (FIG. 5) and the increase in $T_m$ with r is notably less than with 1ab-AuNP, FIG. 2b. Interestingly, for 2ab-AuNP there is no change in either $\lambda_{SPR}$ (FIG. 2c) or $D_h$ (FIG. 2d) with r which collectively suggest that DOX binding to this gold bound duplex is weaker than for 1ab and that the binding mechanism may be non-intercalative in nature.

If 1ab-AuNP is to potentially serve as a carrier for delivering high payloads of drug to a tumor site, it is important to show that DOX can be released from the loaded particle to a receptor target DNA. That this is possible was demonstrated by loading a dialysis membrane with DOX-1ab-AuNP (r=1), exposing the membrane to a solution containing a high concentration of calf thymus DNA (CT-DNA) and after 24 h, measuring the concentration of DOX transferred from particle-DNA to the target CT-DNA outside the membrane (see supporting information). Spectrophotometric analysis showed that ~28% of the DOX originally bound to 1ab-AuNP was transferred to CT-DNA, demonstrating that DOX can be released from particle-DNA and captured by a receptor DNA.

These results show that 1ab-AuNP binds DOX at high affinity sites (5'-TCG), and once these sites are saturated (r~3) drug continues to weakly bind to other regions of the DNA and/or AuNP, increasing AuNP hydrophobicity. Moreover, the particle-bound drug can be transferred to a receptor DNA, raising the possibility that drug delivered by the particle to a cell could be available for interaction with genomic DNA. Aside from simple diffusion of bound drug away from particle DNA, it may be possible to initiate drug release by photothermal melting, apatmer recognition, and/or degradation of the drug-DNA complex by nucleases. These studies are part of our ongoing work to explore the potential of AuNPs as new delivery vehicles for clinically approved anti-cancer drugs.

Example

Experimental Details

All materials, unless otherwise specified, were purchased from Sigma Aldrich. All oligonucleotides, including 1a/2a precursors, 1b/2b, and 1b-CY3 (and excluding CT-DNA) were purchased from Integrated DNA Technologies.

Experimental Design

Nanoparticle Synthesis and DNA-Functionalization (1a/2a-AuNP)

Figure 3:
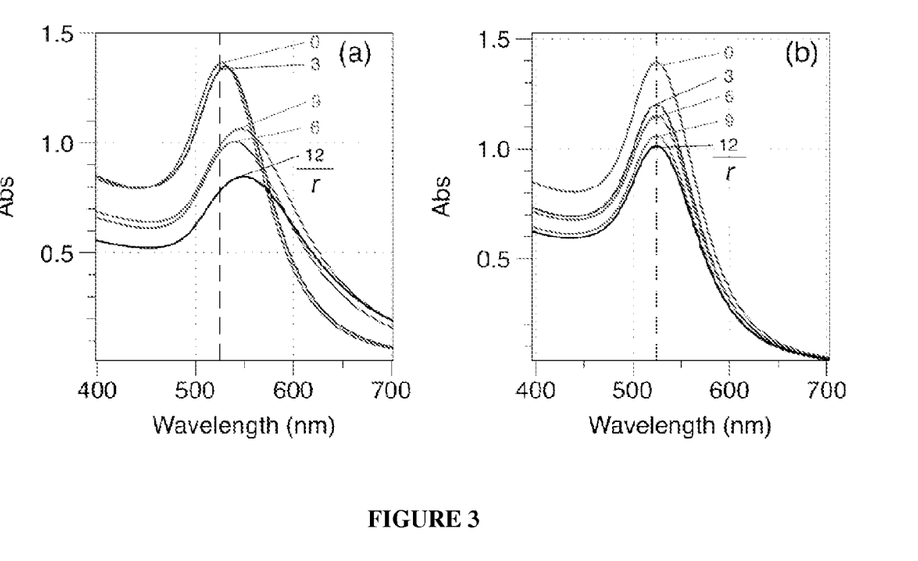
FIG. 3 is a series of graphs showing representative UV-vis spectra for 1ab-AuNP (a) and 2ab-AuNP (b) at DOX loadings of r=[DOX]/[1ab/2ab]=0, 3, 6, 9, 12. ([AuNP]=14 nM, 10 mM Phosphate Buffer, 100 mM NaCl, pH=7.4).
Figure 4:
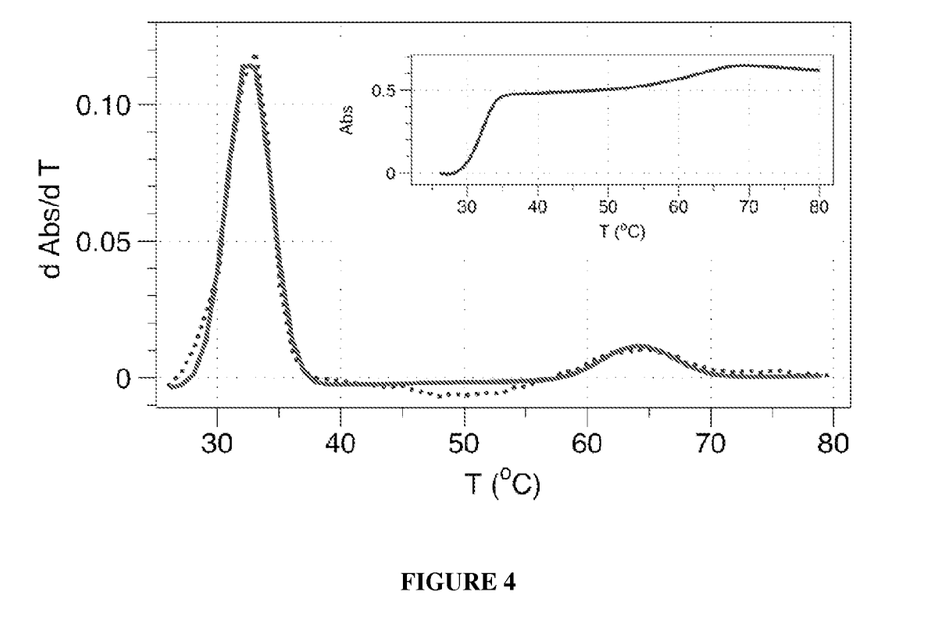
FIG. 4 is a graph of a representative first derivative plot of thermal denaturation of DOX-1ab-AuNP at r=9. Inset: The corresponding thermal denaturation profile. (1° C./min, 10 mM Phosphate Buffer, 100 mM NaCl, pH=7.4).
Figure 5:
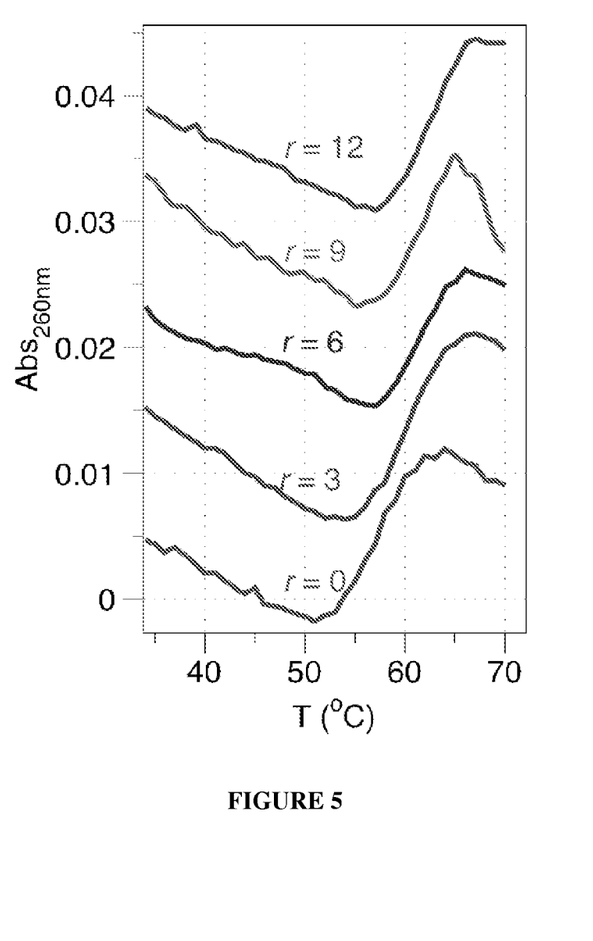
FIG. 5 is a graph of the Thermal denaturation plots for 2ab-AuNP at r=[DOX]/[1ab]=0, 3, 6, 9, 12. r=0-12. Melting profiles have been normalized and off-set for clarity. (1° C./min, 10 mM Phosphate Buffer, 100 mM NaCl, pH=7.4).

The gold nanoparticles (AuNP) with average diameters of 15.5±3.1 nm AuNPs were synthesized by standard citrate reduction method (FIGS. 3-5). Next, the AuNP were functionalized with ssDNA using methods for high DNA coverage (FIG. 5). Briefly, the 1a and 2a, compounds of FIG. 1, were purchased as disulfides, and first reduced using dithiothreitol, to produce 1a/2a (containing a 5'-terminal thiol), which were then purified using a Sephadex G-25 column. Next, the AuNP were incubated with 1a or 2a at 300× molar ratio ([1a]/[AuNP]), and then subjected to the salt aging process (S1, 4). The [1a] and [2a] stock concentrations were determined using UV-visible spectroscopy (UV-vis), based on extinction coefficients, $\epsilon_{260}$=304,800 and 316,900 $M^{-1}cm^{-1}$, respectively. The [AuNP] was similarly determined based on $\epsilon_{525}$=2×10$^8$ $M^{-1}cm^{-1}$.

The 1a-AuNP or 2a-AuNP were then purified via centrifugation. The average DNA loading on each AuNP (~33±2) was estimated based on measurement of DNA uptake, as measured during purification. The number of 1ab molecules per AuNP was later confirmed using fluorescence spectroscopy (4), see below.

DNA-Hybridization (1ab/2ab-AuNP)

In a typical hybridization experiment, 1a- or 2a-AuNP was combined with 100 molar excess of the respective partial complement 1b, or 2b, forming 1ab or 2ab dsDNA functionalized AuNP (1ab-AuNP, 2ab-AuNP). To promote full hybridization, the solution was heated to 60° C., and allowed to cool to room temperature for 1 h. The 1ab- or 2ab-AuNP were then purified of free 1b or 2b via centrifugation. All final 1ab- or 2ab-AuNP was resuspended in PBS (100 mM NaCl, 10 mM Phosphate buffer, pH=7.4). Washing/resuspension was repeated at least three times.

Fluorescence spectroscopy using a dye-modified 1b ssDNA was used to determine the average loading of 1ab on AuNP. Briefly, samples of 1a-AuNP with 1b-CY3 (1b modified by covalent attachment of the fluorescent dye, CY3) as described above were used, except that 1a-AuNP was combined with 9.4 molar excess of 1b-CY3. Following hybridization, each solution was centrifuged, removing the 1ab-Cy3-AuNP, and the supernatant containing excess 1b-CY3 was removed and compared to a concentration calibration curve prepared for 1b-CY3. Each experiment was performed in triplicate. Using this method (4), an average number of 36±1 1ab dsDNA was calculated at each AuNP. Using this value, it was possible to calculate the appropriate number of DOX drugs to add to a known concentration of AuNP, as described next.

Drug Loading and Thermal Denaturation Analysis

Figure 6:
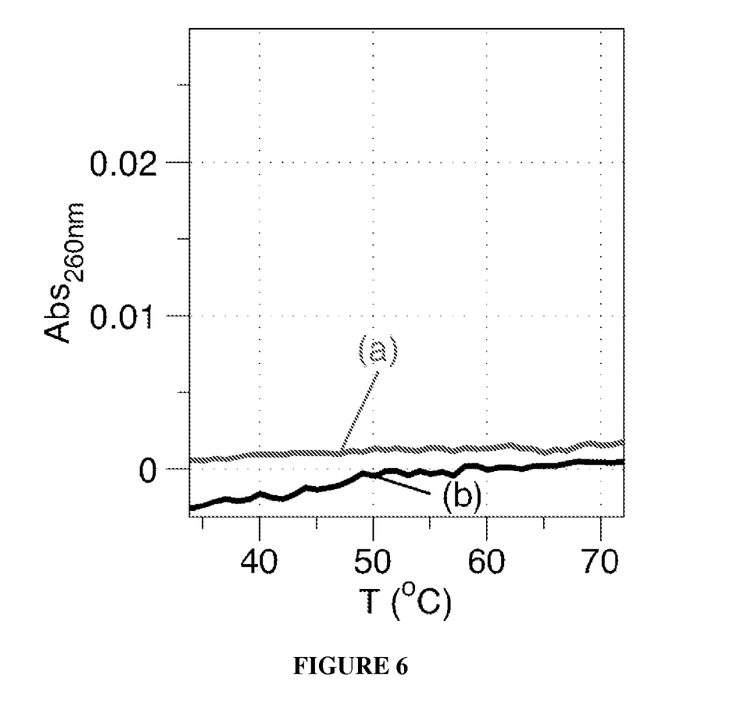
FIG. 6 is a graph of thermal denaturation control studies for DOX (a, r=12, [DOX]=5.9 μM) and DOX-1a-AuNP (b, r=12; [AuNP]=13.7 nM. Cooperative melting in the temperature range of ~55-65° C. is not observed for either control.
Figure 7:
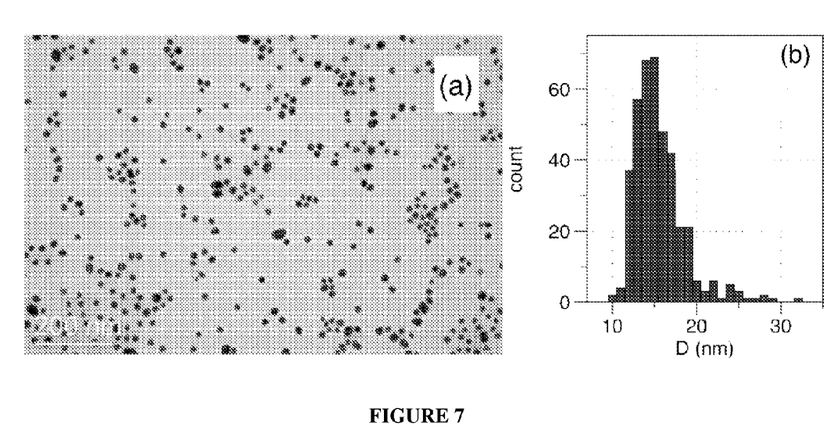
FIG. 7 is a graph of a representative TEM micrograph (a) and statistical analysis (b) for 1a-AuNP with diameter of 15.5±3.1 nm (n=399).

We next utilized the 1ab- or 2ab-AuNP prepared above, with dsDNA-functionalization, for drug (DOX) loading. For each DOX binding and melting experiment, 1ab- or 2ab-AuNP were incubated for 40 min with DOX at specific ratios, r=[DOX]/[1ab/2ab]. In this study, we explored r=0-12, based on the number of 1ab per AuNP, as well as the number of binding sites at each 1ab. Next, each DOX-1ab-AuNP was analyzed via thermal denaturation melting experiments using temperature controlled UV-vis at Abs=260 nm and a heating rate of 1° C./min from 25° C. to 80° C. Each melting temperature was taken as the maximum of a peak-fitted first derivative plot of its corresponding melting curve (using PeakFit® Peak Separation and Analysis Software, V.4.12). The [DOX] was calculated for DOX stock solutions based on $\epsilon_{480}=11,500$ $M^{-1}cm^{-1}$ (FIG. 6).

Drug Release

The monitor the release of DOX bound to the 1ab-AuNP, we employed a transfer dialysis experiment. Briefly, a concentrated solution ([AuNP]=197.3 nM) of DOX-1ab-AuNP (r=1) was placed inside a dialysis membrane (Spectra/Por Biotech regenerated cellulose dialysis membrane, MWCO=15 kD), and the loaded membrane was placed in a $8.53 \times 10^{-4}$ M solution of calf thymus DNA (CT-DNA) in PBS (10 mM phosphate buffer, 100 mM NaCl, pH=7.4) and stirred for 24 h. After this time, a UV-vis spectral analysis of the solution containing CT-DNA showed the characteristic spectrum of DOX bound to DNA. Using, $\epsilon_{505}=6,930$ $M^{-1}cm^{-1}$, (FIG. 6), the [DOX] in the solution containing CT-DNA was calculated and the percentage of particle-bound drug transferred to the CT-DNA outside the membrane was determined to be 27.5%. Two controls, which only deviated from the experimental conditions by the contents of the dialysis membrane, were carried out. A control containing only 1ab-AuNP in the dialysis membrane verified that no AuNP passed through the membrane, and a second control containing only DOX in the dialysis membrane verified that DOX passes through the membrane and binds CT-DNA to produce the spectrum noted in the drug transfer experiment.

Instrumentation

UV-visible Absorption (UV-vis): The UV-vis measurements were collected on a Varian Cary100 Bio UV-vis spectrophotometer between 200-900 nm. The instrument is equipped with an 8-cell automated holder with high precision Peltier heating controller.

Dynamic Light Scattering (DLS): Dynamic Light Scattering (DLS) measurements were collected using a Malvern Zetasizer ZS instrument equipped with a 633 nm laser source, and a backscattering detector at 173°.

Fluorescence Spectroscopy

The PL emission and excitation measurements were collected on a Fluoromax-4 photon counting spectrofluorometer (Horiba Jobin Yvon). The instrument is equipped with a 150 W xenon white light excitation source and computer controlled monochromator. The detector is a R928P high sensitivity photon counting detector that is calibrated to emission wavelength. All PL emission and excitation spectra were collected using both wavelength correction of source intensity and detector sensitivity.

Transmission Electron Microscopy (TEM): TEM measurements were performed on either a FEI T12 Twin TEM operated at 120 kV with a LaB6 filament and Gatan Orius dual-scan CCD camera (Cornell Center for Materials Research), or a JEOL 2000EX instrument operated at 120 kV with a tungsten filament (SUNY-ESF, N.C. Brown Center for Ultrastructure Studies). Particle size was analyzed manually by modeling each qdot as a sphere, with statistical analysis performed using ImageJ software on populations of at least 100 counts.

TABLE 1

Thermal melting temperature, $T_m$, surface plasmon resonance wavelength maximum, $\lambda_{max}$ and dynamic light scattering diameter, $D_h$, of 1ab/2ab-AuNP with [DOX]/[1ab/2ab] = r = 0-12.

| | 1ab-AuNP | | | | 2ab-AuNP | | |
|---|---|---|---|---|---|---|---|
| r | $T_m$ (° C.) | $T_m$ (° C.) | $\lambda_{max}$ (nm) | $D_h$ (nm) | $T_m$ (° C.) | $\lambda_{max}$ (nm) | $D_h$ (nm) |
| 0.0 | | 56.6 | 527 | 30.9 | 58.0 | 525 | 27.5 |
| 1.5 | | 58.9 | 527 | 32.1 | | | |
| 3.0* | 28 | 59.9 | 527 | 32.9 | 60.7 | 525 | 27.0 |
| 4.5 | 28 | 62.1 | 528 | 34.1 | | | |
| 6.0 | 29 | 63.8 | 537 | 34.5 | 61.9 | 525 | 26.9 |
| 7.5 | 30 | 64.9 | 542 | 34.7 | | | |
| 9.0 | 33 | 63.9 | 542 | 34.4 | 62.2 | 525 | 27.0 |
| 10.5 | 30 | 64.7 | 545 | 34.2 | | | |
| 12 | 35 | 65.4 | 547 | 34.6 | 62.9 | 525 | 27.1 |

*r = 3.0 values for 1ab-AuNP are averages of triplicate samples ($T_m$ = 28 ± 2° C., and $T_m$ = 59.9 ± 0.8° C.).

If 1ab-AuNP is to potentially serve as a carrier for delivering high payloads of drug to a tumor site, it is important that DOX can be released from the loaded particle to a receptor target DNA. In addition to DNA melting, we also investigated DOX release to receptor DNA in solution using a dialysis membrane loaded with DOX-1ab-AuNP (at $r_d$=1), and exposed to a solution containing a high concentration of duplex calf thymus DNA (CT-DNA). The dialysis membrane itself serves only to separate the AuNP from DOX for UV-vis analysis. The DOX release, and uptake by CT-DNA was then measured by UV-vis (20) in which we measured the release of DOX from the 1ab-AuNP. In this test, ~28% of DOX was released after only 24 h, demonstrating a significant drug release in a timely manner to a receptor DNA.

Cytotoxicity experiments were performed using neuroblastoma (SK-N-SH) cells under standard conditions in an incubator, using Eagle's minimum essential media (MEM) containing 10% fetal bovine serum (FBS), 100 µg/mL streptomycin, and 100 IU/mL penicillin. Solutions containing free DOX and 1ab-AuNP loaded with DOX at a saturated loading ratio (3 DOX/1ab), were prepared at [DOX]=0.1, 1, 5, and 10 µM, for 24 h exposure, 1 h recovery, in media. Cells were plated in a 96-well microplate, and, following incubation, media was removed, and media containing specified concentrations of drug were added. Following exposure time, media containing drug was removed, and cells were washed with fresh media. Following recovery time, cell viability was determined using the CCK-8 assay. To evaluate the degree of cytotoxicity attributable to the DNA-AuNP in the absence of drug, a control experiment was performed using 1ab-AuNP at an effective [DOX]=0.05, 0.5, 2.5, and 5 μM, for a 48 h exposure, and 1 h recovery time.

In these preliminary cytotoxicity experiments, the DOX-1ab/2ab-AuNP systems produced similar inhibition in comparison to DOX alone. The 1ab-AuNP control was observed to not produce inhibition at any concentrations explored. Interestingly, the DOX-1ab-AuNP was noted to produce a greater percent inhibition at the lowest two [DOX]=0.1 and 1 μM, in comparison to DOX alone, demonstrating the potential of the DOX-1ab-AuNP systems to effectively kill cells at low concentration. The internalization of a single DOX 1ab/2ab-AuNP is perhaps extremely likely to kill a cell when internalized, whereas DOX internalization may result in only a slightly increased likelihood of cell death, and it may take many internalized DOX molecules to kill a cell. Upcoming cytotoxicity experiments will likely clarify the inhibition differences between DOX-1ab/2ab-AuNP and DOX alone.

Collectively, these results demonstrate that DNA-capped nanoparticles can be designed to bind multiple copies of an intercalating drug. The 1ab-AuNP is clearly shown to bind DOX at high affinity sites, which indicated by $T_m$ and $D_h$ elevation. The particle-bound DOX was shown to be released and transferred under mild conditions to a receptor DNA. Preliminary cytotoxicity studies demonstrated similar inhibition of neuroblastoma cells by the DOX-1ab/2ab-AuNP systems as by the drugs alone and slightly elevated inhibition at low concentration. Fluorescence-based kinetic drug transfer experiments are in progress, and are intended to determine the rate and extent of drug release. Other upcoming work includes varying conditions of cytotoxicity studies.

Most clinically used anticancer drugs have relatively narrow therapeutic windows indicating that the distribution of the drug between normal and diseased tissue is small. The present invention provides for multiple copies of certain clinically used anticancer drugs to be attached to particle bound DNA to yield a new type of drug delivery device. When the device is equipped with a vector capable of targeting a cancer cell, it will be possible to direct high copy numbers of drug to tumors. As the gold nanoparticles with attached DNA can be internalized by the cell, the present invention is capable of delivering a high payload of drug specifically to cancer cells, thereby effectively enhancing the therapeutic window of the antitumor agent. An additional attractive feature of the present invention is that since existing clinically used anticancer drugs can be used, FDA approval of the drug which is incorporated into the device, is not required. Implementation of the present invention may require determining the cytotoxicity of the invention toward various cancer cell lines, incorporation of a cellular targeting vector, equipping the device with other DNA binding drugs, and exploring methods of triggering drug release such as degradation of DNA by nucleases and photothermal heating.

The nanoparticle delivery system of the present invention may be adapted to deliver other drugs by tailoring the DNA encoding to accommodate additional chemotherapy drugs, such as actinomycin D (ActD), epirubicin (EPI), idarubicin (IDA), and bleomycin (BLM). The present invention can also incorporate folic acid (FA) and RGB targeting vectors and PEG groups to the dsDNA functionality. A list of the ssDNA sequences having binding affinity for these drugs are shown in Table 1 below.

TABLE 1

DNA sequences required for Drug Intercalation:

| Drug | DNA Encoding (Bold = Drug Binding Site) | bases | # Sites |
|---|---|---|---|
| DOX | 1a = 5'-(HS)-(T)$_{15}$-TGT TCG TAT TCG TAT TCG TC-3' (SEQ. NO. 1) | 35 | 3 |
|  | 1b = 3'-CA AGC ATA AGC ATAAGCAG-5' (SEQ. NO. 2) | 19 |  |
| ActD | 2a = 5'-(HS)-(T)$_{15}$-GA GCT TAGA GCT TAGA GCT T-3' (SEQ. NO. 3) | 35 | 3 |
|  | 2b = 3'-CT CGA ATCT CGA ATCT CGA A-5' (SEQ. NO. 4) | 20 |  |
| EPI | 3a = 5'-(HS)-(T)$_{15}$-TGT TGG TAT TGG TAT TGG TC-3' (SEQ. NO. 5) | 35 | 3 |
|  | 3b = 3'-CA ACC ATA ACC ATA ACC AG-5' (SEQ. NO. 6) | 19 |  |
| IDA | 4a = 5'-(HS)-(T)$_{15}$-GTT TCA GTT TCA GTT TCA GT-3' (SEQ. NO. 7) | 35 | 3 |
|  | 4b = 3'-CAA AGT CAAAGTCAA AGT CA-5' (SEQ. NO. 8) | 20 |  |
| BLM | 5a = 5'-(HS)-(T)$_{15}$-T TGCC ACT TGCC ACT TGCC A-3' (SEQ. NO. 9) | 35 | 3 |
|  | 5b = 3'-AACGG TGAACGG TGA ACGG T-5' (SEQ. NO. 10) | 20 |  |

It should be recognized by those of skill in the art that the oligonucleotides having binding sites for other DNA binding drugs as identified above could be substituted for the doxorubicin specific binding sites to bind those other drugs to the gold nanoparticles of the present invention.

What is claimed is:

1. A drug delivery system, comprising:
   a gold nanoparticle;
   a first nucleic acid molecule covalently linked to said gold nanoparticle and having multiple binding sites having a high affinity for a drug; and
   a second, complementary nucleic acid molecule hybridized to said first nucleic acid molecule to form a double stranded nucleic acid molecule;
   wherein said first nucleic acid molecule comprises a sequence selected from the group consisting of SEQ ID NO. 1, SEQ ID NO. 3, SEQ ID NO. 5, SEQ ID NO. 7, and SEQ ID NO. 9.

2. The system of claim 1, wherein said drug is doxorubicin.

3. The system of claim 1, wherein said first nucleic acid molecule has at least three binding sites having a high affinity for doxorubicin.

4. The system of claim 3, further comprising a doxorubicin molecule bound to each of said multiple binding sites.

5. The system of claim 3, wherein said first nucleic acid molecule is longer than said second, complementary nucleic acid molecule.

6. The system of claim 1, wherein said gold nanoparticle has a diameter of about 15.5 nanometers.

7. A method of forming a drug delivery system, comprising the steps of:
   covalently linking a first nucleic acid molecule including multiple binding sites having a high affinity for a drug to a gold nanoparticle, wherein said first nucleic acid molecule comprises a sequence selected from the group consisting of SEQ ID NO. 1, SEQ ID NO. 3, SEQ ID NO. 5, SEQ ID NO. 7, and SEQ ID NO. 9; and
   hybridizing a second, complementary nucleic acid molecule to said first nucleic acid molecule to form a double-stranded nucleic acid molecule.

8. The method of claim 7, wherein said drug is doxorubicin.

9. The method of claim 7, wherein the step of covalently linking a first nucleic acid molecule to a gold nanoparticle further comprises covalently linking a plurality of said first nucleic acid molecules to said gold nanoparticle.

10. The method of claim 9, wherein the step of hybridizing a second, complementary nucleic acid molecule to said first nucleic acid molecule to form a double-stranded nucleic acid molecule further comprises hybridizing a plurality of said second, complementary nucleic acid molecules to said plurality of said first nucleic acid molecules to form a plurality of said binding sites.

11. The method of claim 10, further comprising a doxorubicin molecule bound to each of said multiple binding sites.

12. The method of claim 10, wherein each of said plurality of first nucleic acid molecules is longer than each of said second nucleic acid molecules.

13. The method of claim 10, wherein said gold nanoparticle has a diameter of about 15.5 nanometers.

14. A method of delivering a drug to a patient, comprising the steps of:
proviing at least one gold nanoparticle covalently linked to a plurality of first nucleic acid molecules, each of which is hybridized with a plurality of second, complementary nucleic acid molecules to form a plurality of double-stranded nucleic acid molecules, wherein each double-stranded nucleic acid molecule has multiple binding sites with a high affinity for a drug molecule and wherein said first nucleic acid molecule comprises a sequence selected from the group consisting of SEQ ID NO. 1, SEQ ID NO. 3, SEQ ID NO. 5, SEQ ID NO. 7, and SEQ ID NO. 9; and
binding a plurality of said drugs molecules to said binding sites to form a drug loaded nanoparticle.

15. The method of claim 14, further comprising the step of administering the drug loaded nanoparticle to a patient.

16. The method of claim 14, wherein said drug is doxorubicin.

17. The method of claim 14, wherein said gold nanoparticle has a diameter of about 15.5 nanometers.

18. The system of claim 1, wherein said first nucleic acid molecule comprises SEQ ID NO. 1.

19. The system of claim 1, further comprising doxorubicin intercalated to said binding sites, wherein said intercalated doxorubicin and said first nucleic acid molecule are characterized by a release rate of about 28 percent over 24 hours.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Drug binding site

<400> SEQUENCE: 1
tgttcgtatt cgtattcgtc                                               20

<210> SEQ ID NO 2
<211> LENGTH: 19
<212> TYPE: DNA
<213> ORGANISM: Artificial Sequence
<220> FEATURE:
<223> OTHER INFORMATION: Drug binding site

<400> SEQUENCE: 2
caagcataag cataagcag                                                19

<210> SEQ ID NO 3
<211> LENGTH: 20
<212> TYPE: DNA
<213> ORGANISM: Artificial Sequence
<220> FEATURE:
<223> OTHER INFORMATION: Drug binding site

<400> SEQUENCE: 3
gagcttagag cttagagctt                                               20

<210> SEQ ID NO 4
<211> LENGTH: 20
<212> TYPE: DNA
<213> ORGANISM: Artificial Sequence
<220> FEATURE:
<223> OTHER INFORMATION: Drug binding site

<400> SEQUENCE: 4
ctcgaatctc gaatctcgaa                                               20

<210> SEQ ID NO 5
<211> LENGTH: 20
<212> TYPE: DNA
<213> ORGANISM: Artificial Sequence
<220> FEATURE:
<223> OTHER INFORMATION: Drug binding site

<400> SEQUENCE: 5
tgttggtatt ggtattggtc                                               20

<210> SEQ ID NO 6
<211> LENGTH: 19
<212> TYPE: DNA
<213> ORGANISM: Artificial Sequence
<220> FEATURE:
<223> OTHER INFORMATION: Drug binding site

<400> SEQUENCE: 6
caaccataac cataaccag                                                19

<210> SEQ ID NO 7
<211> LENGTH: 20
<212> TYPE: DNA

```
<213> ORGANISM: Artificial Sequence
<220> FEATURE:
<223> OTHER INFORMATION: Drug binding site

<400> SEQUENCE: 7
gtttcagttt cagtttcagt                                              20

<210> SEQ ID NO 8
<211> LENGTH: 20
<212> TYPE: DNA
<213> ORGANISM: Artificial Sequence
<220> FEATURE:
<223> OTHER INFORMATION: Drug binding site

<400> SEQUENCE: 8
caaagtcaaa gtcaaagtca                                              20

<210> SEQ ID NO 9
<211> LENGTH: 20
<212> TYPE: DNA
<213> ORGANISM: Artificial Sequence
<220> FEATURE:
<223> OTHER INFORMATION: Drug binding site

<400> SEQUENCE: 9
ttgccacttg ccacttgcca                                              20

<210> SEQ ID NO 10
<211> LENGTH: 20
<212> TYPE: DNA
<213> ORGANISM: Artificial Sequence
<220> FEATURE:
<223> OTHER INFORMATION: Drug binding site

<400> SEQUENCE: 10
aacggtgaac ggtgaacggt                                              20
```